United States Patent [19]

Glassman et al.

[11] Patent Number: 5,698,022
[45] Date of Patent: Dec. 16, 1997

[54] LANTHANIDE/PHOSPHORUS PRECURSOR COMPOSITIONS FOR MOCVD OF LANTHANIDE/PHOSPHORUS OXIDE FILMS

[75] Inventors: Timothy E. Glassman, Danbury; Paul V. Chayka, New Milford, both of Conn.

[73] Assignee: Advanced Technology Materials, Inc., Danbury, Conn.

[21] Appl. No.: 696,478

[22] Filed: Aug. 14, 1996

[51] Int. Cl.$^6$ .............. C23C 16/00; C07F 5/00
[52] U.S. Cl. ........... 106/287.18; 556/19; 556/21; 556/22; 556/24; 427/226; 427/248.1; 427/255; 427/255.3
[58] Field of Search .......... 106/287.18; 556/19, 556/21, 22, 24; 427/226, 248.1, 255, 255.3

[56] References Cited

U.S. PATENT DOCUMENTS

| | | | |
|---|---|---|---|
| 4,880,670 | 11/1989 | Erbil | 427/226 |
| 4,882,206 | 11/1989 | Erbil | 427/229 |
| 4,915,988 | 4/1990 | Erbil | 427/252 |
| 4,927,670 | 5/1990 | Erbil | 427/255.3 |
| 4,992,305 | 2/1991 | Erbil | 427/252 |
| 5,064,802 | 11/1991 | Stevens et al. | 502/155 |
| 5,352,488 | 10/1994 | Spencer et al. | 427/250 |

OTHER PUBLICATIONS

Sato, S.; Hasegawa, M.; Sodesawa, T.; Nozaki, F. "Silica-supported Boron Phosphate Catalyst Prepared by Chemical Vapor Deposition." in *Bull. Chem. Soc. Jpn.* (1991) 64, 268.

Deschanvres, J.L.; Vaca, J. M.; Joubert, J. C. "Thin Films of Zirconia–Phosphate Glasses Deposited by an Aerosol CVD Process." in *J. Phys. IV* (1995) 5, C5/1029.

*Primary Examiner*—David Brunsman
*Attorney, Agent, or Firm*—Steven J. Hultquist; Janet R. Elliott

[57] ABSTRACT

A precursor composition useful for vapor deposition formation of lanthanide metal/phosphorus oxide films, comprising a precursor compound selected from the group consisting of: (i) adducts of the formula $MA_3(L)_x$; (ii) phosphido complexes of the formulae $M(PR_3)_3$ or $M(PR_3)_3L_x$; and (iii) disubstituted phosphate complexes of the formulae $A_2M(O_2P(OR)_2)$, $AM(O_2P(OR)_2)_2$, and $M(O_2P(OR)_2)_3$, wherein: x is from 1 to 5, A=Cp or β-diketonate, Cp=cyclopentadienyl, methylcyclopentadienyl, or TMS-cyclopentadienyl, $R=C_1–C_8$ alkyl, and L=a phosphorus-containing ligand selected from the group consisting of phosphine, phosphine oxide, phosphite, phosphate, and 1,2-bis(dimethoxyphosphoryl)benzene, subject to the provisos that: when x is 2 or greater, each L may be the same as or different from the other L; and when the precursor compound is a β-diketonate compound of formula (i), L is not phosphate or phosphine oxide. The precursor composition may be employed for forming a lanthanide metal/phosphorus oxide film on a substrate, by depositing a lanthanide metal/phosphorus material on the substrate from the lanthanide metal/phosphorus precursor composition in vaporized form, and incorporating oxygen in the lanthanide metal/phosphorus material to form the lanthanide metal/phosphorus oxide film on the substrate.

23 Claims, No Drawings

5,698,022

LANTHANIDE/PHOSPHORUS PRECURSOR COMPOSITIONS FOR MOCVD OF LANTHANIDE/PHOSPHORUS OXIDE FILMS

BACKGROUND OF THE INVENTION

1. Field of the Invention

The present invention relates to transition metal/phosphorus precursor-compounds and compositions for metalorganic chemical vapor deposition formation of lanthanide metal/phosphorus oxide films, and to composites, devices, and other structures comprising such films, as well as methods of making and using such compounds and compositions.

2. Description of the Related Art

The implementation of ceramic matrix composites has not significantly occurred in turbine engines or power generation systems due to the lack of proper coatings for the reinforcement fibers and the absence of a commercially useful method to deposit them. Lanthanum phosphate ($LaPO_4$) has arisen as an interface thin film material which could provide the characteristics needed for composites to perform as required.

In addition, thin films of metal phosphates have a wide variety of other unrelated applications. Although the art has evolved means to deposit high quality coatings, suitable precursors for MOCVD of $LaPO_4$ are not available. Applications of thin film metal phosphates include power generation systems, aircraft engines and hazardous waste incinerators. The economic reward of using such thin film metal phosphate coatings approaches $4 Billion/year in potential energy savings and 0.5 million tons of annual $NO_x$ reduction in industrial air emissions.

Research in fiber/matrix interfaces has successfully demonstrated enhanced brittle composite toughness for weak, compliant, sliding, or debonding fiber coatings. However, established coatings will not endure the high temperature applications without oxidizing or reacting with, and degrading properties of, the fiber and/or matrix. The present lack of interfacial films with the appropriate debonding/sliding behavior and a high degree of mechanical and environmental stability, is a major obstacle in the development of composites which will meet design requirements. Several researchers have used theoretical modeling to identify candidate interface coatings.

One coating which has shown tremendous promise is $LaPO_4$. Coatings of lanthanum-phosphorus-oxide have been demonstrated via metalorganic chemical vapor deposition (MOCVD), and fundamental experiments have supported this modeling. However, fiber coating technology, required for sample preparation and testing, has not kept pace with these efforts. Development efforts have suffered from: (i) a lack of data for precursors of metals and nonmetals, (ii) difficulties in applying high quality coatings, particularly to continuous multifilament fiber tows, and (iii) the high costs associated with the limited fiber coatings that have been available.

An established competitive process for applying fiber coatings is to employ sol-gel formation of such coatings. Ceramic fibers are dipped in a bath of a solution containing the coating precursors, removed and treated to gel the coating. The precursors are then pyrolyzed to form the desired coating. Although such a process has a potential advantage of higher throughput than MOCVD, coating thickness is low, requiring multiple coating runs. Also, bonding of filaments to each other is frequent and very difficult to control, and coating texture tends to be very rough and powdery which makes the coated fiber difficult to handle. Lastly, coating uniformity over the fiber bundle may be poor, leading to weakened sites.

$LaPO_4$ also has been proposed as a coating on sapphire fibers in polycrystalline $Al_2O_3$ matrixes by dipping in a slurry/dispersion of $LaPO_4$ in alcohol solution and firing at 1400° C. for 1 hr. The ceramic phosphate coating (monazites) form a weak bonding interlayer with the ceramic fiber. The interphase material allows debonding and frictional sliding between the constituents of the composites, inhibits crack growth across the interface, and the composites are morphologically stable to high temperature oxidizing environments. However, as a result of the inability to control thickness, this method is not appropriate for applying $LaPO_4$ coatings to fibers for production scale processing.

The deposition of metal phosphate thin films has received little attention in the open literature. Noncrystalline chromium, molybdenum and tungsten phosphates have been deposited using the low valent, phosphine adducts $M(CO)_5(PH_3)$. However, the scarcity of known phosphine adducts of lanthanide metals renders this methodology of limited use. In addition, the toxicity and pyrophoric nature of phosphine discourages commercialization of a process based on this class of precursors. The safer phosphorus-containing precursor trialkylphosphate $OP(OMe)_3$ has been used for the CVD of phosphate glasses, such as phosphosilicates and boron phosphate $BPO_4$.

Trialkylphosphates and β-diketonate metal complexes have also been used to deposit transition metal phosphates. Aerosol CVD has been used to deposit phosphate films from (i) $Zr(acac)_4$ (acac=MeC(O)CHC(O)Me) and $OP(OPh)_3$, and (ii) $Ga(acac)_3$ and $OP(OBu)_3$. $LaPO_4$ films have been formed on sapphire fibers by coating with a dispersion in alcohol and then embedding in an $\alpha$-$Al_2O_3$ matrix and firing at 1400° C.

A variety of phosphines and their oxidation products exist, including: phosphates $OP(OR)_3$, phosphites $P(OR)_3$, phosphine oxides $OPR_3$ and phosphines $PR_3$. The adducts $La(thd)_3[OP(OR)_3]_x$ and $La(thd)_3[OPR_3]_x$ ($PR_3=PMe_3$, $PMe_2Bu$, $Pbu_3$) and $OP(octyl)_3$ complex fall apart into its separate components with ease, making the CVD process very dependent on the deposition parameters. However, only a few percent of phosphorus is incorporated when using phosphine oxide adducts. Phosphine oxide adducts are also known for fluorinated lanthanum β-diketonates, for instance: $La(hfac)_3(OPR_3)_2$. CVD processes utilizing such phosphine oxide adducts are also very dependent on the deposition parameters. While this dependence could be considered to add flexibility, it also makes process reproducibility much more difficult.

The incorporation of lanthanum into thin films has received growing attention due to its use in $Pb_{1-x}La_xTiO_3$ (PLT) and $Pb_{1-x}La_x(Zr_{1-y}Ti_y)O_3$ (PLZT) ferroelectrics, $La_{2-x}M_xCuO_4$ (M=Ca, Sr, Ba; x<0.5) high temperature superconductors (HTSC), $LaCuO_2$ piezoelectrics, $LaAlO_3$ buffer layers and $La_{1-x}Ca_xMnO_3$ collosal magnetoresistance (CMR) materials. Sputtering and pulsed laser deposition of lanthanum oxide-containing films have been pursued, but are not suitable techniques for the coating of fibers. Materials that have been used for MOCVD growth of lanthanum oxide-containing materials include $La(\eta\text{-}C_5H_4R)_3$ (R=H, Me, $CHMe_2$), and $La(thd)_3$ (thd=2,2,6,6-tetramethyl-3,5-heptanedionate). $La(thd)_3$ is one of the most commonly used precursors; however, process reproducibility is difficult since it is a solid precursor often supplied as a hydrated material which changes composition with time in the delivery bubbler. Process reproducibility is also complicated by any impurity in the source reagent, so that the reagent should be of high purity for optimal results. The reported melting point of La(thd)$_3$ spans 222°–229° C.; however, a closer examination by thermogravimetric analysis/differential scanning calorimetry (TGA/DSC) has shown that anhydrous material actually undergoes a solid-solid phase transition at 193° C. and melts at 262° C. and does not vaporize until 240°–315° C. at atmospheric pressure. The use of TGA/DSC has yielded evidence that conversion of La(thd)$_3$ to the oxide is a feasible process. In an oxygen atmosphere, thermal oxidation yields La$_2$O$_3$ cleanly.

SUMMARY OF THE INVENTION

The present invention relates to compositions and methods for forming lanthanide metal/phosphorus oxide films (e.g., LaPO$_4$) on substrates.

In one compositional aspect of the invention, there is provided a precursor composition useful for vapor deposition formation of lanthanide metal/phosphorus oxide films, comprising a precursor compound selected from the group consisting of:

(i) adducts of the formula MCp$_3$(L)$_x$;

(ii) phosphido complexes of the formula M(PR$_3$)$_3$ or M(PR$_3$)$_3$L$_x$; and (iii) disubstituted phosphate complexes of the formulae A$_2$M(O$_2$P(OR)$_2$), AM(O$_2$P(OR)$_2$)$_2$, and M(O$_2$P(OR)$_2$)$_3$, wherein:
 x is from 1 to 5,
 A=Cp or β-diketonate;
 M=a lanthanide metal;
 Cp=cyclopentadienyl, or substituted cyclopentadienyl,
 R=C$_1$–C$_8$ alkyl, and
 L=a phosphorus-containing ligand selected from the group consisting of phosphine, phosphine oxide, phosphite, phosphate, and 1,2-bis (dimethoxyphosphoryl)benzene,
 subject to the provisos that:
  when x is 2 or greater, each L may be the same as or different from the other L; and
  when the precursor compound is a β-diketonate compound of formula (i), L is not phosphate or phosphine oxide.

The substituted cyclopentadienyl ligand may comprise as the substituent(s) thereof alkyl substituent, e.g., a C$_1$–C$_4$ alkyl moiety, or a substituted or unsubstituted silyl moiety. Two illustrative substituted Cp ligands are trimethylsilylcyclopentadienyl and methylcyclopentadienyl.

The precursor composition described above may further comprise a solvent for the precursor compound, e.g., a solvent such as tetrahydrofuran, butyl acetate, tetraglyme, diethylene triamine, or mixtures thereof, with the proviso that the solvent does not contain tetraglyme when L is phosphine.

In another aspect, the invention relates to a method of forming a lanthanide metal/phosphorus oxide film on a substrate, comprising depositing a lanthanide metal/phosphorus material on the substrate from a vapor-phase lanthanide metal/phosphorus precursor composition comprising a precursor compound selected from the group consisting of:

(i) adducts of the formula MCp$_3$(L)$_x$;

(ii) phosphido complexes of the formula M(PR$_3$)$_3$ or M(PR$_3$)$_3$L$_x$; and (iii) disubstituted phosphate complexes of the formulae A$_2$M(O$_2$P(OR)$_2$), AM(O$_2$P(OR)$_2$)$_2$, and M(O$_2$P(OR)$_2$)$_3$, wherein:
 x is from 1 to 5,
 A=Cp or β-diketonate;
 M=a lanthanide metal;
 Cp=cyclopentadienyl, or substituted cyclopentadienyl,
 R=C$_1$–C$_8$ alkyl, and
 L=a phosphorus-containing ligand selected from the group consisting of phosphine, phosphine oxide, phosphite, phosphate, and 1,2-bis (dimethoxyphosphoryl)benzene,
 subject to the provisos that:
  when x is 2 or greater, each L may be the same as or different from the other L; and
  when the precursor compound is a β-diketonate compound of formula (i), L is not phosphate or phosphine oxide; and incorporating oxygen in the lanthanide metal/phosphorus material to form the lanthanide metal/phosphorus oxide film on the substrate.

In such method, the step of depositing a lanthanide metal/phosphorus material on the substrate from a vapor-phase lanthanide metal/phosphorus precursor composition preferably comprises chemical vapor deposition of said lanthanide metal/phosphorus material from said precursor composition. The step of incorporating oxygen in the lanthanide metal/phosphorus material to form the lanthanide metal/phosphorus oxide film on the substrate, may be carried out by exposing the deposited lanthanide metal/phosphorus material to an oxygen-containing gas subsequent to deposition of the lanthanide metal/phosphorus material, or alternatively by depositing said material on the substrate in an oxygen-containing environment. For example, in the substrate environment, oxygen may be present in the form of N$_2$O or oxygen may be present in a precursor ligand species in such environment.

Other aspects and features of the invention will be more fully apparent from the ensuing disclosure and appended claims.

DETAILED DESCRIPTION OF THE INVENTION, AND PREFERRED EMBODIMENTS THEREOF

The compositions of the invention include a precursor compound selected from the group consisting of:

(i) adducts of the formula MCp$_3$(L)$_x$;

(ii) phosphido complexes of the formula M(PR$_3$)$_3$ or M(PR$_3$)$_3$L$_x$; and (iii) disubstituted phosphate complexes of the formulae A$_2$M(O$_2$P(OR)$_2$), AM(O$_2$P(OR)$_2$)$_2$, and M(O$_2$P(OR)$_2$)$_3$, wherein:
 x is from 1 to 5,
 A=Cp or β-diketonate;
 M=a lanthanide metal;
 Cp=cyclopentadienyl, or substituted cyclopentadienyl,
 R=C$_1$–C$_8$ alkyl, and
 L=a phosphorus-containing ligand selected from the group consisting of phosphine, phosphine oxide, phosphite, phosphate, and 1,2-bis (dimethoxyphosphoryl)benzene,
 subject to the provisos that:
  when x is 2 or greater, each L may be the same as or different from the other L; and when the precursor compound is a β-diketonate compound of formula (i), L is not phosphate or phosphine oxide.

Each of these precursor compounds is described in turn below. As used herein, the term "lanthanide metal" encompasses the metals of the lanthanide series of the Periodic Table, including the following metal species: La, Ce, Y, Nd, Pr, Pm, Sm, Eu, Gd, Tb, Dy, Ho, Er, Tm, Yb, and Lu.

Lanthanide Metal Cp Adducts

The adducts of the lanthanide metal β-diketonates or cyclopentadienyls can be prepared by addition of one or two equivalents of the desired ligand to either La(thd)$_3$, in accordance with reaction (1a) below, or alternatively to MCp$_3$ in accordance with reaction (1b) below.

  (1a)

  (1b)

Table I below sets out some phosphorus-containing ligands L for M(Cp)$_3$(L)$_x$.

TABLE 1

Phosphorus-containing ligands L for M(thd/Cp)$_3$(L)$_x$

| Ligand L | Formula | Structure |
|---|---|---|
| Monodentate Phosphines | PR$_3$ | 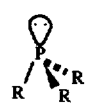 |
| Bidentate Phosphines | R$_2$PCH$_2$CH$_2$PR$_2$ | 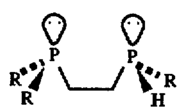 |
| Phosphates | OP(OR)$_3$ | 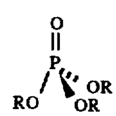 |
| Phosphine oxides | OPR$_3$ | 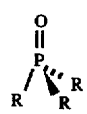 |
| Phosphites | P(OR)$_3$ | 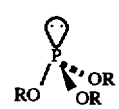 |
| 1,2-Bis(dimethoxy-phosphoryl)-benzene | C$_6$H$_4$[PO(OMe)$_2$]$_2$ | 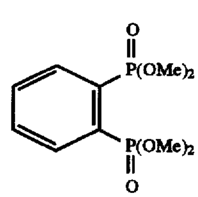 |

In contrast to phosphine oxide OPR$_3$ and phosphate OP(OR)$_3$ β-diketonate adducts, there is some evidence that LaCp$_3$ adducts may be oligomeric in structure. Illustrative examples of the ligands tabulated in Table 1 include monodentate phosphines such as P(n-Bu)$_3$, bidentate phosphines such as Me$_2$PCH$_2$CH$_2$PMe$_2$, and phosphites such as P(OMe)$_3$. These ligands and the potentially chelating 1,2-bis(dimethoxy-phosphoryl)benzene C$_6$H$_4$[PO(OMe)$_2$]$_2$ ligand may be usefully employed with MCp$_3$ centers (coordinating moieties). The 1,2-bis(dimethoxy-phosphoryl)benzene ligand has a structurally rigid phenyl backbone for preventing facile dissociation of the ligand thereby enhancing phosphorus incorporation in the deposition product.

Lanthanide Metal Phosphido Complexes

Direct incorporation of the phosphorus in the coordinated complex, in a form less susceptible to dissociation, may substantially increase the incorporation of phosphorus in the deposited lanthanide metal/phosphorus material. Materials such as La(PR$_2$)$_3$ may be dimeric or Lewis base adducts. Homoleptic dialkylphosphido complexes are known for virtually every transition metal and include the following lanthanide species: Ln(P(SiMe$_3$)$_2$)$_3$(thf)$_2$ (Ln=Tm, Nd) and Ln(PPh$_2$)$_2$(thf)$_4$ (Ln=Sm, Yb). The only reported lanthanum diphosphide of which we are aware is the structurally characterized La[P(2-C$_6$H$_4$OMe)$_2$]$_3$.

Oxidation of M(PR$_2$)$_3$ may be employed to yield lanthanide metal phosphates such as LaPO$_4$. Excess phosphorus may be extruded as P$_2$R$_4$, a common thermolysis by-product.

The phosphido complexes may be formed in a manner analogous to the synthesis of the related lanthanide alkoxide Ln(OR)$_3$ complexes. The most basic reaction is the salt metathesis reaction using anhydrous [LaCl$_3$]$_x$ which is commercially available and LiPR$_2$ as shown in reaction (2a) below. Occasionally problems with lanthanides arise due to the formation of mixed metal salt complexes. In these cases either the byproduct LiCl or excess starting material LiPR$_2$ coordinates to the desired product to yield materials such as Li[La(PR$_2$)$_3$Cl] or Li[La(PR$_2$)$_4$]. This problem often can be solved by the reacting LaI$_3$(thf)$_x$ with potassium salts of the desired phosphide KPR$_2$ as shown in reaction (2b) below. The greater solubility of the iodide salt LaI$_3$(thf)$_x$ over anhydrous [LaCl$_3$]$_x$ allows for more rapid completion of reactions, while the covalent nature of KI renders it less likely than the ionic LiCl to complex with the desired product. An alternative method to avoid complex mixed metal salts is the displacement of amine reactions from elimination amides such as La(N(SiMe$_3$)$_2$)$_3$ or La(N-iPr$_2$)$_3$(thf) as shown in reaction 2c below.

  (2a)

  (2b)

  (2c)

Disubstituted Phosphate Complexes L$_x$M[O$_2$P(OR)$_2$]$_{3-x}$

Much of the problem with previously reported approaches to incorporation of phosphorus in La-P-O films relates to the facile loss of the neutral phosphine ligand. Synthesis of phosphides may be complicated by the material's sensitivity to air and moisture, problems which are overcome by utilization of ligands containing both oxygen and phosphorus, in the disubstituted phosphate complexes of the formula L$_x$M[O$_2$P(OR)$_2$]$_{3-x}$.

These disubstituted phosphate complexes may be formed by reaction of (R)$_2$PO(OH) where R is alkyl, e.g., i-butyl, propyl, or aminoalkenyl, with lanthanide metal compounds such as La[O$_2$P(t-Bu)$_2$]$_3$, A$_2$La[O$_2$P(t-Bu)$_2$] and ALa[O$_2$P(t-Bu)$_2$]$_2$, where A=Cp or β-diketonate.

The precursor composition described above may further comprise a solvent for the precursor compound, e.g., a solvent such as tetrahydrofuran, butyl acetate, tetraglyme, diethylene triamines, or mixtures thereof, with the proviso that the solvent does not contain tetraglyme when L is phosphine. Examples of solvent formulations which may be usefully employed include mixtures of tetrahydrofuran and tetraglyme, e.g., in a 9:1 ratio by weight.

In the precursors of the invention comprising a phosphine moiety as the phosphorus-containing ligand thereof, the phosphine may be monodentate or bidentate in character. In general, the compounds of the invention may be employed to provide a desired stoichiometric ratio of lanthanide metal:phosphorus, e.g., 1:1, 1:2, or 2:1, by selection of an appropriate compound or compounds from among the group comprising: (i) adducts of the formula $MA_3(L)_x$; (ii) phosphido complexes of the formula $M(PR_3)_3$ or $M(PR_3)_3L_x$; and (iii) disubstituted phosphate complexes of the formula $A_2M(O_2P(OR)_2)_2$, $AM(O_2P(OR)_2)_2$, and $M(O_2P(OR)_2)_3$.

The organo substituents R of the lanthanide metal/phosphorus precursors of the invention include $C_1$–$C_8$ alkyl, preferably $C_1$–$C_4$ alkyl, as well as other suitable hydrocarbyl groups.

The precursor compositions of the invention may be usefully employed in forming a lanthanide metal/phosphorus oxide film on a substrate, by depositing a lanthanide metal/phosphorus material on the substrate from a vapor-phase lanthanide metal/phosphorus precursor composition of the invention, and oxidizing the lanthanide metal/phosphorus material to form the lanthanide metal/phosphorus oxide film on the substrate. The deposition may comprise any suitable type of chemical vapor deposition (CVD), including low pressure CVD and/or assisted CVD techniques (e.g., plasma, laser, etc.), atmospheric pressure CVD, etc., on any appropriate substrate.

The lanthanide metal/phosphorus precursor composition of the invention may be utilized in solid form as a single source solid reagent, in a bubbler or other suitable device for forming a source vapor for the deposition of the lanthanide metal/phosphorus material. Alternatively, the lanthanide metal/phosphorus precursor composition may be dissolved in any suitable solvent and vaporized for passage to the CVD reactor or other deposition locus, using a liquid delivery and vaporization system, such as that disclosed in Kirlin et al. U.S. Pat. No. 5,536,323 issued Jul. 16, 1996, the disclosure of which is hereby incorporated herein in its entirety.

In the method of the invention, the step of oxidizing the lanthanide metal/phosphorus material to form the lanthanide metal/phosphorus oxide film on the substrate, may be carried out by exposing the deposited lanthanide metal/phosphorus material to an oxygen-containing gas, such as pure oxygen, $N_2O$, or an oxygen/inert gas mixture, subsequent to deposition of the lanthanum/phosphorus material, or alteratively by depositing such material on the substrate in an oxygen-containing environment. Oxygen may be furnished in the deposition environment by the solvent used as a carrier medium for the precursor, or the precursor composition itself may contain the requisite oxygen for the formation of an oxide film. The present invention may employ any of such modes of incorporating oxygen in the deposited lanthanum/phosphorus material. The deposition and oxygen-incorporation steps may be carried out at any suitable process conditions, as may be readily determined without undue experimentation by those skilled in the art.

In a particularly preferred end use application, the precursor composition and method of the invention may be employed to manufacture high performance ceramic composites, by forming a lanthanide metal phosphate coating on fiber or other discontinuous reinforcement media, e.g., of sapphire or other glass, metal, or ceramic medium, which is subsequently incorporated in a composite matrix material whose continuous phase comprises a high performance ceramic or cermet material.

While the invention has been described herein with reference to specific illustrative aspects and embodiments thereof, it will be appreciated that the utility of the invention is not thus limited, but rather extends to variations, modifications and other embodiments of the specifically disclosed features.

For example, although the invention has been described most specifically in reference to the deposition of lanthanum/phosphorus films, it will be appreciated that the invention may also be practiced with other lanthanide metals than lanthanum per se.

The invention is therefore to be correspondingly broadly construed and interpreted, as encompassing within its scope all such variations, modifications and embodiments.

What is claimed is:

1. A precursor composition useful for vapor deposition formation of lanthanide metal/phosphorus oxide films, comprising a precursor compound selected from the group consisting of:
   (i) adducts of the formula $MA_3(L)_x$;
   (ii) phosphido complexes of the formula $M(PR_3)_3$ or $M(PR_3)_3L_x$; and
   (iii) disubstituted phosphate complexes of the formulae $A_2M(O_2P(OR)_2)$, $AM(O_2P(OR)_2)_2$, and $M(O_2P(OR)_2)_3$,
   wherein:
   x is from 1 to 5,
   A=Cp or β-diketonate;
   M=a lanthanide metal;
   Cp=cyclopentadienyl, or substituted cyclopentadienyl,
   R=$C_1$–$C_8$ alkyl, and
   L=a phosphorus-containing ligand selected from the group consisting of phosphine, phosphine oxide, phosphite, phosphate, and 1,2-bis(dimethoxyphosphoryl)benzene,
   subject to the provisos that:
   when x is 2 or greater, each L may be the same as or different from the other L; and
   when the precursor compound is a β-diketonate compound of formula (i), L is not phosphate or phosphine oxide.

2. A precursor composition according to claim 1, wherein said precursor compound is an adduct of the formula $MA_3(L)_x$.

3. A precursor composition according to claim 2, wherein L is a monodentate phosphine.

4. A precursor composition according to claim 2, wherein L is a bidentate phosphine.

5. A precursor composition according to claim 1, wherein said precursor is an adduct of the formula $MCp_3(L)_x$.

6. A precursor composition according to claim 1, wherein said precursor is an adduct of the formula $La(β\text{-diketonate})_3(L)_x$.

7. A precursor composition according to claim 1, wherein said precursor compound is a phosphido complex of the formula $La(PR_3)_3$.

8. A precursor composition according to claim 1, wherein said precursor compound is a disubstituted phosphate complex of the formula $A_2La(O_2P(OR)_2)$.

9. A precursor composition according to claim 1, further comprising a solvent for said precursor compound.

10. A precursor composition according to claim 9, wherein the solvent is selected from the group consisting of tetrahydrofuran, butyl acetate, tetraglyme, diethylene triamines, and mixtures thereof, with the proviso that the solvent does not contain tetraglyme or diethylene triamines when L is phosphine.

11. A precursor composition according to claim 1, wherein R is $C_1$–$C_4$ alkyl.

12. A method of forming a lanthanide metal/phosphorus oxide film on a substrate, comprising depositing a lanthanide metal/phosphorus material on the substrate from a vapor-phase lanthanide metal/phosphorus precursor composition comprising a precursor compound selected from the group consisting of:

(i) adducts of the formula $LaA_3(L)_x$;

(ii) phosphido complexes of the formula $La(PR_3)_3$ or $La(PR_3)_3L_x$; and (iii) disubstituted phosphate complexes of the formulae $A_2La(O_2P(OR)_2)$, $ALa(O_2P(OR)_2)_2$, and $La(O_2P(OR)_2)_3$, wherein:

x is from 1 to 5,

A=Cp or β-diketonate,

Cp=cyclopentadienyl, methylcyclopentadienyl, or TMS-cyclopentadienyl,

R=$C_1$–$C_8$ alkyl, and

L=a phosphorus-containing ligand selected from the group consisting of phosphine, phosphine oxide, phosphite, phosphate, and 1,2-bis(dimethoxyphosphoryl)benzene, subject to the provisos that:

when x is 2 or greater, each L may be the same as or different from the other L; and when the precursor compound is a β-diketonate compound of formula (i), L is not phosphate or phosphine oxide; and incorporating oxygen in the lanthanum/phosphorus material to form the lanthanum/phosphorus oxide film on the substrate.

13. A method according to claim 12, further comprising forming the vapor-phase lanthanide metal/phosphorus precursor composition by vaporization of a liquid solution of said precursor compound.

14. A method according to claim 12, wherein the step of incorporating oxygen in said lanthanide metal/phosphorus material to form the lanthanide metal/phosphorus oxide film on the substrate, comprises a step selected from those including: exposing the deposited lanthanide metal/phosphorus material to an oxygen-containing gas subsequent to deposition of the lanthanide metal/phosphorus material; depositing said material on the substrate in an oxygen-containing fluid environment; and incorporating oxygen in the lanthanide metal/phosphorus material from an oxygen-containing component of said vapor-phase lanthanide metal/phosphorus precursor composition.

15. A method according to claim 12, wherein the step of incorporating oxygen in said lanthanide metal/phosphorus material to form the lanthanide metal/phosphorus oxide film on the substrate, comprises depositing said material on the substrate in an oxygen-containing environment.

16. A method according to claim 12, wherein said precursor compound is an adduct of the formula $MA_3(L)_x$.

17. A method according to claim 12, wherein said precursor is an adduct of the formula $MCp_3(L)_x$.

18. A method according to claim 12, wherein said precursor is an adduct of the formula $La(\beta\text{-diketonate})_3(L)_x$.

19. A method according to claim 12, wherein said precursor compound is a phosphido complex of the formulae $M(PR_3)_3$ or $M(PR_3)_3L_x$.

20. A method according to claim 12, wherein said precursor compound is a disubstituted phosphate complex of the formulae $A_2M(O_2P(OR)_2)$, $AM(O_2P(OR)_2)_2$, and $M(O_2P(OR)_2)_3$.

21. A method according to claim 12, wherein the precursor composition comprises a solvent for said precursor compound.

22. A method according to claim 21, wherein the solvent is selected from the group consisting of tetrahydrofuran, butyl acetate, tetraglyme, diethylene triamines, and mixtures thereof, with the proviso that the solvent does not contain tetraglyme or diethylene triamines when L is phosphine.

23. A method according to claim 12, wherein R is $C_1$–$C_4$ alkyl.

* * * * *